United States Patent [19]

Suzuki

[11] Patent Number: 4,506,098
[45] Date of Patent: Mar. 19, 1985

[54] PROCESS FOR THE PREPARATION OF 2,6-DIALKYLANILINE FROM 1-NITROALKENE

[75] Inventor: Shigeto Suzuki, San Francisco, Calif.

[73] Assignee: Chevron Research Company, San Francisco, Calif.

[21] Appl. No.: 280,426

[22] Filed: Jul. 6, 1981

[51] Int. Cl.³ .............................................. C07C 87/50
[52] U.S. Cl. .................................... 564/305; 564/416; 564/462
[58] Field of Search ........................................ 564/305

[56] References Cited

U.S. PATENT DOCUMENTS

| | | | |
|---|---|---|---|
| 3,361,818 | 1/1968 | Barker .................................. | 564/305 |
| 3,427,355 | 2/1969 | Le Maistre et al. ............ | 564/305 X |
| 4,271,091 | 6/1981 | Grasselli et al. ..................... | 564/305 |

OTHER PUBLICATIONS

Kataev et al., "Jour. Gen. Chem. USSR", vol. 23, pp. 413–417, (1953).

*Primary Examiner*—Robert V. Hines
*Attorney, Agent, or Firm*—S. R. LaPaglia; T. G. DeJonghe; C. J. Caroli

[57] ABSTRACT

A process for the preparation of 2,6-dialkylaniline which comprises the reaction of a 1-nitroalkene with a 1,3-alkadiene to form a dialkyl nitrocyclohexene adduct and subsequent reaction of the resulting adduct with hydrogen in the presence of a hydrogenation catalyst to form the corresponding dialkylcyclohexyl amine, followed by dehydrogenation with aqueous ammonia in the presence of a dehydrogenation catalyst.

15 Claims, No Drawings

PROCESS FOR THE PREPARATION OF 2,6-DIALKYLANILINE FROM 1-NITROALKENE

BACKGROUND OF THE INVENTION

This invention is concerned with an improved process for the preparation of 2,6-dialkylaniline which comprises the reaction of a 1-nitroalkene with a 1,3-alkadiene to form a dialkylnitrocyclohexene adduct and subsequent reaction of the resulting adduct with hydrogen in the presence of a hydrogenation catalyst to form the corresponding dialkylcyclohexyl amine, followed by dehydrogenation with aqueous ammonia in the presence of a dehydrogenation catalyst.

One method of preparing 2,6-dialkylaniline is by the amination of hydroxyaromatics. U.S. Pat. No. 3,931,298 describes a process for the preparation of aromatic amines by the reaction of hydroxy-substituted aromatic compounds with ammonia in the presence of a catalytic amount of a cyclohexanone and in contact with a hydrogen transfer catalyst.

U.S. Pat. No. 3,960,962 describes a related process wherein aromatic hydroxy compounds are converted to the corresponding aromatic amine by reaction with ammonia in the presence of a cyclohexanone promoter and a catalyst comprising metallic palladium bonded to a phosphinated polystyrene resin.

In U.S. Pat. No. 3,965,182 aromatic amines are made by reacting a phenol with aluminum nitride and either ammonia or a primary or secondary amine.

U.S. Pat. No. 3,801,642 is concerned with a process for replacing an aromatic hydroxyl group with an amine group by forming a metal aryloxide from the corresponding aromatic hydroxy compound and reacting the metal aryloxide with ammonia or a primary or secondary amine in the presence of a Friedel-Crafts catalyst.

U.S. Pat. No. 4,125,560 describes the direct amination of phenols with amines by the ammonolysis of phenols in a liquid phase under pressure with an aqueous ammonia solution containing a catalytic amount of an ammonium salt.

U.S. Pat. No. 3,219,704 describes the preparation of aromatic amines by the condensation of six-membered alicyclic ketones and ammonia compounds with a dehydrogenation catalyst, wherein the molar portion of the ketone is at least substantially equal to the ammonia compound.

In U.S. Pat. No. 3,442,950 aminated benzenes are prepared by catalytically reacting a cyclohexanol with an aminating agent. When cyclohexanone is present in the cyclohexanol component, the reaction is initiated in the presence of one mole of hydrogen per mole of cyclohexanone.

An article by E. G. Kataev and P. S. Matveeva in the Journal of General Chemistry, U.S.S.R., volume 23, pages 413–417 (1953) describes the reaction of piperylene with nitroamylene to form 2-methyl-6-n-propyl-1-nitrocyclohex-3-ene, but does not teach the preparation of the corresponding aromatic amine.

Dialkylanilines, and in particular 2,6-dialkylanilines, are useful intermediates for a variety of compounds having herbicidal and fungicidal activity.

SUMMARY OF THE INVENTION

It has now been found that 2,6-dialkylanilines, wherein each alkyl group contains 1–4 carbon atoms, may be prepared in high yield by a process which comprises the steps of:

(a) contacting a 1-nitroalkene having 3–6 carbon atoms with a 1,3-alkadiene having 5–8 carbon atoms at a temperature of from about 40° C. to about 200° C. and at a pressure of from about 0 psig to about 1000 psig to form a 3,5-dialkyl-4-nitro-cyclohexene adduct;

(b) contacting said adduct with hydrogen at a temperature of from about 0° C. to about 200° C. and at a pressure of from about 0 psig to about 1500 psig in the presence of a hydrogenation catalyst to form a 2,6-dialkylcyclohexyl amine; and (c) contacting said amine with aqueous ammonia at a temperature of from about 200° C. to about 300° C. and at a pressure of from about 500 psig to about 1500 psig in the presence of a dehydrogenation catalyst.

Preferable 2,6-dialkylanilines prepared by this method include those wherein each alkyl group contains 1–2 carbon atoms, such as 2-methyl-6-ethylaniline and 2,6-diethylaniline. Most preferably, the 2,6-dialkylaniline is 2,6-dimethylaniline.

The 1-nitroalkenes suitable for use in the process of the present invention may contain 3–6 carbon atoms, preferably 3 or 4 carbon atoms. An especially preferred 1-nitroalkene is 1-nitropropene. A particularly advantageous method for the preparation of 1-nitroalkenes is described in my application, Ser. No. 280,427, and now U.S. Pat. No. 4,384,149 filed concurrently herewith. According to this method, a 1-alkene is reacted with dinitrogen tetroxide in the presence of oxygen and an ether solvent to form an alkene-dinitrogen tetroxide adduct, which is subsequently heated in the presence of sodium fluoride and an inert gas to form 1-nitroalkene.

The 1-nitroalkene is reacted with a 1,3-alkadiene of 5–8 carbon atoms, preferably 5 or 6 carbon atoms. 1,3-Pentadiene is the most preferred alkadiene. The reaction may be carried out with or without a solvent at a temperature from about 40° C. to about 200° C., preferably from about 110° C. to about 150° C., and a pressure from about 0 psig to about 1000 psig, preferably from about 100 psig to about 300 psig. Generally about 0.5 to 8 moles of 1,3-alkadiene are utilized per mole of 1-nitroalkene and the use of about 3 moles of 1,3alkadiene per mole of 1-nitroalkene is preferred. A free radical inhibitor, such as tert-butylcatechol, may be added to inhibit polymerization of the 1-nitroalkene.

The 3,5-dialkyl-4-nitrocyclohexene thus formed is subjected to catalytic hydrogenation to give the corresponding 2,6-dialkylcyclohexyl amine, which is catalytically dehydrogenated with aqueous ammonia. Crude nitrocyclohexene adduct as a bottoms product may be used for the successive steps without prior purification.

The usual well-known hydrogenation-dehydrogenation catalysts may be used in both the hydrogenation and dehydrogenation steps, among which are catalysts containing one or more elements of Group VIII of the Periodic Table as metal or oxide. In general, hydrogenation catalysts also function as dehydrogenation catalysts and the same catalyst may be utilized in both steps of the present process. Examples of suitable catalysts include platinum, palladium, nickel, cobalt, rhodium, ruthenium, iridium, osmium and mixtures thereof. Copper, molybdenum and chromium may also be utilized as the catalyst. For the purposes of the present invention the preferred catalyst is palladium.

The active component of the catalyst may be used alone or in combination with a support. Examples of suitable supports include carbon, alumina, silica, kieselguhr, aluminum silicates and the like.

Although the hydrogenation step of the present invention may be carried out in mixed liquid-vapor phase, generally it is preferred to carry out the reaction in the liquid phase. Typically the hydrogen remains in gaseous phase except for dissolved hydrogen. Only small excesses of hydrogen are necessary. Large excess amounts of hydrogen may be used to aid contacting and for cooling purposes.

Suitable pressures during hydrogenation are between about 0 and 1500 psig, preferably between 100 and 500 psig. Suitable hydrogenation reaction temperatures are 0° to 200° C., preferably 100° to 150° C. As is conventionally practiced, excess molar amounts of hydrogen are present in the reaction zone to improve the reaction rate and extent.

The dehydrogenation of the 2,6-dialkylcyclohexyl amine is carried out in the presence of about 0.1 to 20, and preferably 1 to 4 moles of ammonia per mole of cyclohexyl amine. Suitable pressure during dehydrogenation are between about 500 psig and 1500 psig, preferably between 500 and 1000 psig. Suitable dehydrogenation reaction temperatures are 200° to 300° C., preferably 210° to 280° C.

The following examples are provided to illustrate the invention in accordance with the principles of this invention but are not to be construed as limiting the invention in any way except as indicated by the appended claims.

EXAMPLES

EXAMPLE 1

A 200 ml capacity, stainless steel reactor was charged with piperylene 61.2 g (0.90 mol), 1-nitropropene 26.1 g (0.30 mol), and t-butylcatechol 0.3 g. The reactor was sealed, pressured to 100 psig with nitrogen at room temperature, and heated at 140°–144° C. for 45 minutes while the reaction mixture was stirred magnetically (maximum pressure, 188 psig). The product was analyzed by gas chromatogram (FFAP column) showing 72% conversion based on 1-nitropropene to 2,6-dimethyl-1-nitrocyclohex-3-ene with better than 95% selectivity. The pure dimethyl-nitrocyclohexene was distilled at 30°–35° C./0.03 mmHg (distilled yield 72%), and the structure was confirmed by its NMR spectrum.

EXAMPLE 2

A 300 ml capacity, stainless steel reactor was charged with piperylene 122.9 g (1.807 mol), 1-nitropropene 43.42 g (0.499 mol), and t-butylcatechol 0.60 g. The reactor was sealed, pressured to 200 psig with nitrogen at room temperature, and heated at 138° C. for 2 hours while the reaction mixture was stirred magnetically (maximum pressure 320 psig). The analysis of the product by gas chromatogram (5% FFAP) showed better than 99% reaction of 1-nitropropene to almost exclusively the dimethyl-nitrocyclohexene. A distillation at 0.11 mmHg gave 72.43 g of the nitrocyclohexene corresponding to 93.4 mol % yield.

EXAMPLE 3

The same reactor used in Example 2 was charged with the dimethyl-nitrocyclohexene 80.22 g (0.52 mol), and 5% Pd metal supported on carbon 5.86 g. The hydrogenation was conducted at 100°–150° C. and 1000 psig $H_2$ pressure for about 9 hours. The product was analyzed by gas chromatogram (FFAP column) showing >99% conversion and 80% yield of 2,6-dimethylcyclohexyl amine with the b.p. 65° C./0.06 mmHg.

EXAMPLE 4

A 300 ml capacity Monel reactor was charged with 2,6-dimethylcyclohexyl amine 51.99 g (0.44 moles), 28% aqueous ammonia 60.7 g, and 5% Pd metal supported on carbon 6.0 g. The reactor was cooled in a Dry Ice-acetone bath, flushed with hydrogen, and heated at 250° C. for 60 minutes while the bomb contents were magnetically stirred. Cooling of the bomb to room temperature showed the generation of 187 psig hydrogen, which was vented out. The heating, cooling and degassing cycling was repeated 2 more times, and approximately 0.16 moles hydrogen gas in total was generated. Analyses of the product by gas chromatogram (5% FFAP) showed 28% conversion of the amine to 2,6-dimethylaniline and intermediate dehydrogenation products with respective selectivities of 37% and 60%. The selectivity to 2,6-dimethylaniline was 93% when the intermediates dehydrogenation products were included as starting material in the selectivity calculation since the intermediates were convertible to 2,6-dimethylaniline. The only other byproduct of this dehydrogenation was 2,6-xylenol in about 6% selectivity.

EXAMPLE 5

A 300 ml capacity, stainless steel reactor was charged with 2,6-dimethyl-1-nitrocyclohexene 31.0 g (0.02 mol), and 5% Pd metal supported on carbon 2.0 g. The reactor was sealed, and stirred at room temperature for 2 hours under 100 psig $H_2$ pressure, and then the temperature and $H_2$ pressure were gradually raised to 150° C. and 500 psig respectively during the period of 35 hours. At the end of this period, the reaction mixture was essentially pure 2,6-dimethylcyclohexylamine. The reactor was cooled and vented, and 28% aqueous ammonia 25 g was added. The reactor was resealed, flushed with $H_2$, stirred at 250° C. for about 2 hours, cooled to room temperature, and excess $H_2$ generated (186 psig) was vented. The heating-cooling-venting cycle was repeated 8 times. Analyses of the final product by gas chromatogram as before showed 96% conversion of the cyclohexyl amine to 2,6-dimethyl aniline, 2,6-xylenol, and intermediate dehydrogenation products with respective selectivities of 53%, 9% and 30%.

What is claimed is:

1. A process for the preparation of 2,6-dialkylaniline wherein each alkyl group contains 1–4 carbon atoms which comprises the steps of:
   (a) contacting a 1-nitroalkene having 3–6 carbon atoms with a 1,3-alkadiene having 5–8 carbon atoms at a temperature of from about 40° C. to about 200° C. and at a pressure of from about 0 psig to about 1000 psig to form a 3,5-dialkyl-4-nitrocyclohexene adduct;
   (b) contacting said adduct with hydrogen at a temperature of from about 0° C. to about 200° C. and at a pressure of from about 0 psig to about 1500 psig in the presence of a hydrogenation catalyst to form a 2,6-dialkylcyclohexyl amine; and
   (c) contacting said amine with aqueous ammonia at a temperature of from about 200° C. to about 300° C. and at a pressure of from about 500 psig to about 1500 psig in the presence of a dehydrogenation catalyst.

2. A process in accordance with claim 1, wherein said 1-nitroalkene contains 3–4 carbon atoms.

3. A process in accordance with claim 2, wherein said 1-nitroalkene is 1-nitropropene.

4. A process in accordance with claim 1, wherein said 1,3-alkadiene contains 5–6 carbon atoms.

5. A process in accordance with claim 4, wherein said 1,3-alkadiene is 1,3-pentadiene.

6. A process in accordance with claim 1, wherein said hydrogenation catalyst is palladium.

7. A process in accordance with claim 1, wherein said dehydrogenation catalyst is palladium.

8. A process in accordance with claim 1, wherein the reaction of the 1-nitroalkene with 1,3-alkadiene is carried out at a temperature of about 110° C. to about 150° C. and a pressure of about 100 psig to about 300 psig.

9. A process in accordance with claim 1, wherein the reaction of the cyclohexene adduct is carried out at a temperature of about 100° C. to about 150° C. and a pressure of about 100 psig to about 500 psig.

10. A process in accordance with claim 1, wherein the reaction of the cyclohexyl amine is carried out at a temperature of about 210° C. to about 280° C. and a pressure of about 500 psig to about 1000 psig.

11. A process in accordance with claim 1, wherein about 3 moles of 1,3alkadiene are employed per mole of 1-nitroalkene.

12. A process for the preparation of 2,6-dimethylaniline which comprises the steps of:

(a) contacting 1-nitropropene with 1,3-pentadiene at a temperature of about 40° C. to about 200° C. and a pressure of about 0 psig to about 1000 psig to form 3,5-dimethyl-4-nitro-cyclohexene;

(b) contacting said 3,5-dimethyl-4-nitro-cyclohexene with hydrogen at a temperature of about 0° C. to about 200° C. and a pressure of about 0 psig to about 1500 psig in the presence of a palladium catalyst to form 2,6-dimethylcyclohexyl amine; and (c) contacting said 2,6-dimethylcyclohexyl amine with aqueous ammonia at a temperature of about 200° C. to about 300° C. and a pressure of about 500 psig to about 1500 psig in the presence of a palladium catalyst.

13. A process in accordance with claim 12, wherein the reaction of 1-nitropropene and 1,3-pentadiene is carried out at a temperature of about 110° C. to about 150° C. and a pressure of about 100 psig to about 300 psig.

14. A process in accordance with claim 12, wherein the reaction of 3,5-dimethyl-4-nitro-cyclohexene is carried out at a temperature of about 100° C. to about 150° C. and a pressure of about 100 psig to about 500 psig.

15. A process in accordance with claim 12, wherein the reaction of 2,6-dimethylcyclohexyl amine is carried out at a temperature of about 210° C. to about 280° C. and a pressure of about 500 psig to about 1000 psig.

* * * * *